(12) United States Patent  (10) Patent No.: US 8,721,638 B2
Deutscher et al.  (45) Date of Patent: May 13, 2014

(54) GAS SENSING SURGICAL DEVICE AND METHOD OF USE

(71) Applicants: Edward Martin Deutscher, Safety Harbor, FL (US); Frank Anthony Vassallo, II, Safety Harbor, FL (US)

(72) Inventors: Edward Martin Deutscher, Safety Harbor, FL (US); Frank Anthony Vassallo, II, Safety Harbor, FL (US)

( * ) Notice: Subject to any disclaimer, the term of this patent is extended or adjusted under 35 U.S.C. 154(b) by 0 days.

(21) Appl. No.: 13/644,202

(22) Filed: Oct. 3, 2012

(65) Prior Publication Data

US 2014/0031814 A1 Jan. 30, 2014

Related U.S. Application Data

(60) Provisional application No. 61/677,285, filed on Jul. 30, 2012.

(51) Int. Cl.
 *A61B 18/14* (2006.01)
(52) U.S. Cl.
 USPC ............................................. 606/42; 606/34
(58) Field of Classification Search
 USPC .................. 606/32, 38, 42; 607/98, 115
 See application file for complete search history.

(56) References Cited

U.S. PATENT DOCUMENTS

| 5,217,457 | A | 6/1993 | Delahuerga et al. |
| 5,312,327 | A | 5/1994 | Bales et al. |
| 5,575,789 | A | 11/1996 | Bell et al. |
| 5,865,788 | A | 2/1999 | Edwards et al. |
| 6,382,207 | B1 | 5/2002 | Giuffre et al. |
| 7,291,145 | B2 * | 11/2007 | Seid ................................. 606/34 |
| 7,296,571 | B2 | 11/2007 | Foltz et al. |
| 7,445,619 | B2 | 11/2008 | Auge, II et al. |
| 7,601,150 | B2 | 10/2009 | Farin |
| 7,771,422 | B2 * | 8/2010 | Auge et al. ....................... 606/41 |
| 2006/0058784 | A1 * | 3/2006 | Gedebou ........................ 606/45 |
| 2006/0069387 | A1 * | 3/2006 | Gedebou ........................ 606/45 |
| 2008/0319441 | A1 * | 12/2008 | Seid ............................... 606/42 |
| 2010/0121163 | A1 * | 5/2010 | Vestel et al. ................... 600/316 |

* cited by examiner

*Primary Examiner* — Michael Peffley
*Assistant Examiner* — Thomas Giuliani
(74) *Attorney, Agent, or Firm* — The Concept Law Group, P.A.; Scott D. Smiley; Mark C. Johnson

(57) ABSTRACT

A handheld surgical assembly has a body, a first end, a second end, and a body length separating the first and second ends, an energy input and output, the energy output located at the first end of the body, the assembly also having a sensor that is coupled to the handheld surgical assembly, in fluid communication with an outside environment, and operable to identify a plurality of gases, with the assembly additionally having an electronic circuit system communicatively coupled to the sensor, the electronic circuit system being operable, upon the identification of at least one of the plurality of gases by the sensor, to control the energy output from the handheld surgical device.

9 Claims, 7 Drawing Sheets

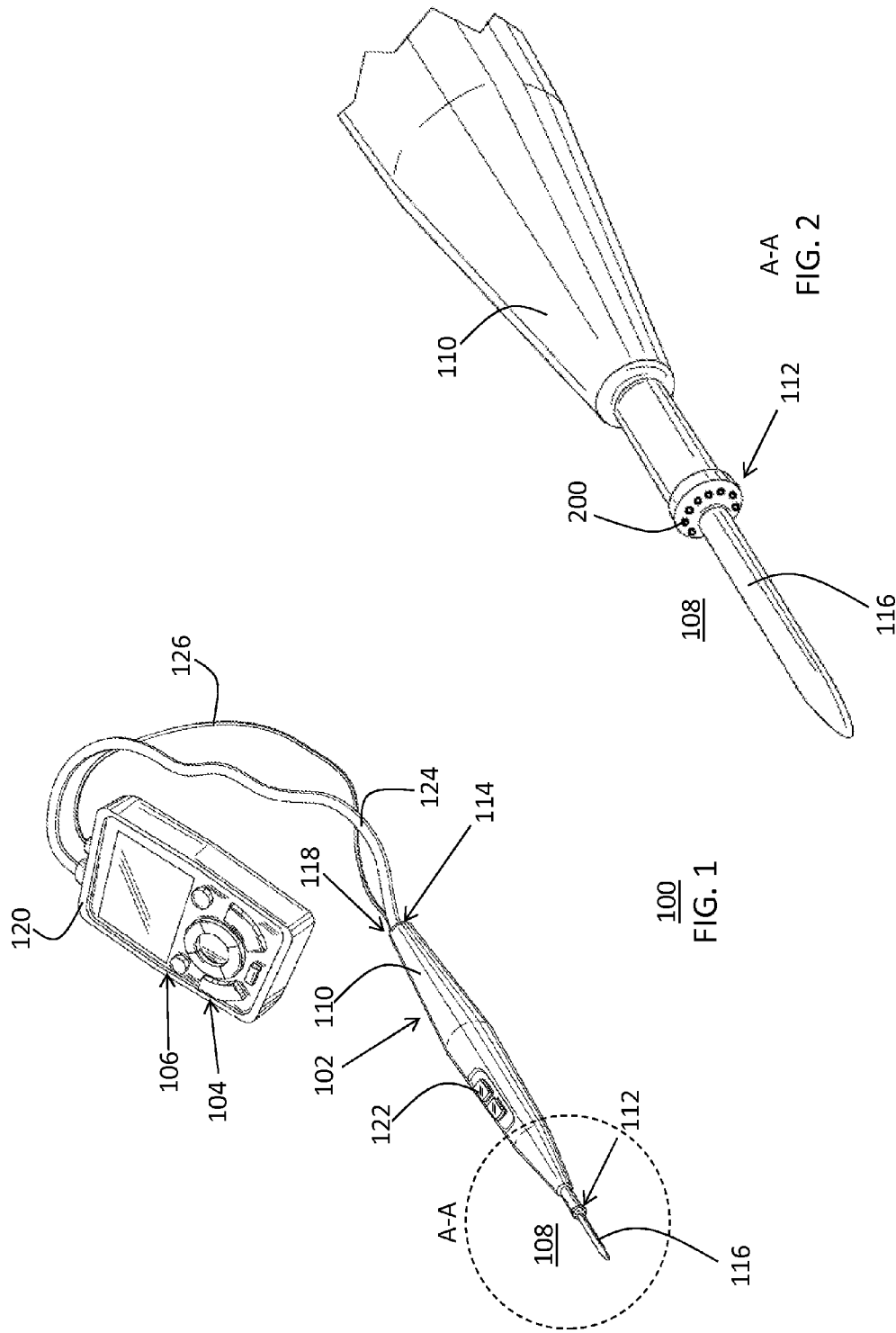

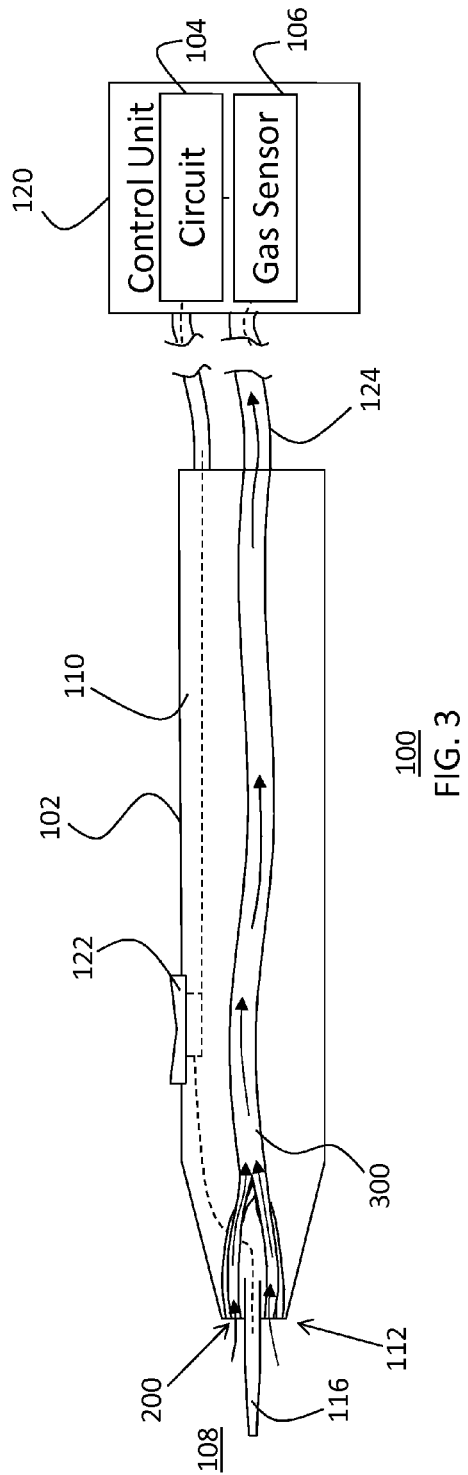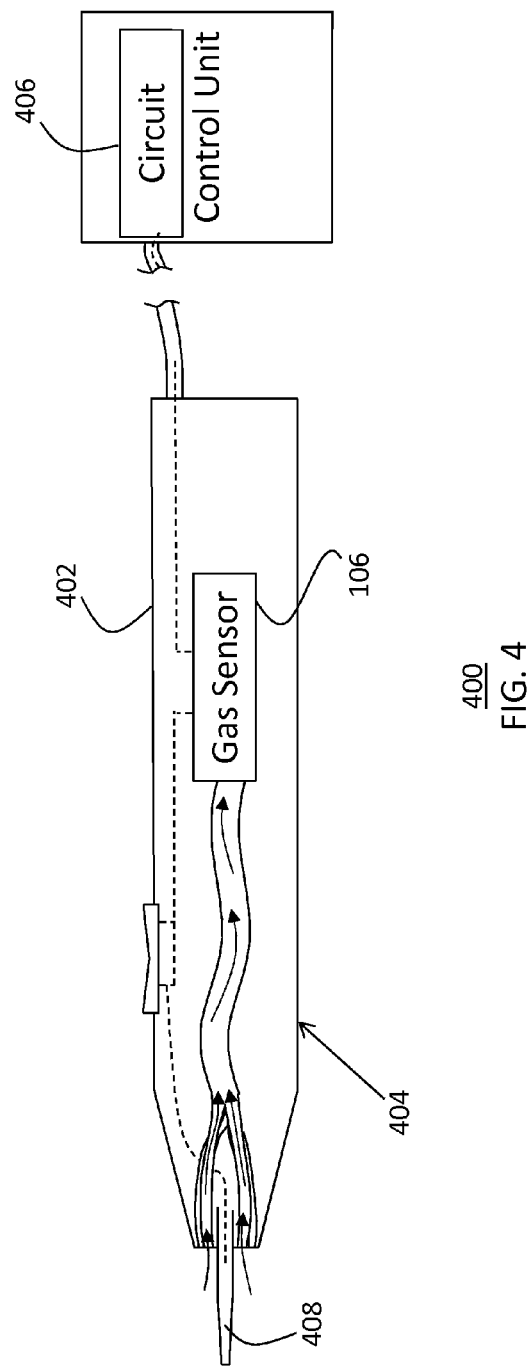

GAS SENSING SURGICAL DEVICE AND METHOD OF USE

CROSS-REFERENCE TO RELATED APPLICATION

This application claims priority to U.S. Provisional Application No. 61/677,285, titled "A Gas Sensing Surgical Device and Method Therefore" and filed on Jul. 30, 2012, which is hereby incorporated by reference in its entirety herein.

FIELD OF THE INVENTION

The present invention relates generally to electrical medical devices, and, more particularly, relates to any electrical medical devices that are operable to identify gases.

BACKGROUND OF THE INVENTION

Advancements are consistently sought in the medical field to improve the quality and care of patients. Many of these advances involve the use of electronic devices and equipment. Many of those devices and equipment are used in surgical or diagnostic settings. This is extremely problematic for patients, physicians, hospitals and others in the medical fields, as the electrical charges and emissions of energy from these devices may cause fires and localized explosions. In fact, the United States Food and Drug Administration (FDA) estimates that approximately 600 surgical fires occur in the United States each year. Many of these explosions traumatically affect patients and/or physicians, leading to disfigurement, scarring, and other injuries. They also expose medical facilities and physicians to civil liability.

In order for these fires or combustions to occur, three requirements must be satisfied (also known as the fire triangle). These requirements include ignition (energy or heat source), a fuel source, and an oxidizer. During medical procedures, electrical medical devices are often utilized. These medical devices, such as electrical surgical units (ESUs), e.g., cautery, diathermy, lasers, ultrasound, fiber-optic light sources and others emit energy at their point-of-use, thereby providing an "ignition" to a fire or combustion. Specifically, ESUs often generate sparks, or induce enough heat at their point-of-use, to cause combustion. "Fuel sources" encountered during surgical procedures include flammable gases and vapors from isopropyl alcohol and other alcohol-based surgical preparations used for sterilization of surgical sites prior to procedures. These substances may saturate and persist in surgical drapes, gowns, gauze and other items commonly found in an operating environment. Furthermore, many of the gases associated with anesthesia to limit or control a patient's pain, or to render a patient unconscious, are flammable. Invariably, these gases are administered to the facial region of a patient often exposing the head, face, throat, airway, and neck to severe damage should a fire or explosion occur. These gases may also disperse and linger under partial, or total body surgical drapes, exposing areas of the patient remote from the head to the risk of severe burns from fires or explosions. Once combustion of these gases or vapors occurs, especially in an oxygen rich surgical environment, there are an abundance of additional fuel sources such as surgical gauze, disposable drapes, gowns, the patient's own hair or skin, and other operating/procedure room materials which may combust or catch on fire.

"Oxidizers," such as oxygen or nitrous oxide (which decomposes to nitrogen and oxygen), create the third element of the fire triangle and may act as accelerants. Oxidizers are routinely administered to patients during surgical procedures involving any type of sedation or anesthesia. While greater amounts of oxygen in environments increase the probability of fires or explosions, even normal oxygen levels found in typical atmospheric environments, e.g., air-conditioned/heated//climate controlled medical facilities, are sufficient to support fires or explosions. Some known devices and methods have attempted to contain oxygen in patients' airways to reduce the risk of combustion. Unfortunately, the oxygen commonly escapes and is found at, or near, sites where ESUs and other energy-emitting devices are used, and thus acts as an accelerant for fires and explosions when flammable gases or vapors are present. Moreover, these devices do not utilize response indicators from any other elements of the fire triangle, such as fuel sources, to prevent combustions. As such, these devices and methods would be ineffective against fires or explosions that may occur within normal oxygen levels found in surgical environments.

Moreover, most, if not all, known medical devices attempting to prevent combustions do not have the ability to adequately and efficiently detect gases. As mentioned, these gases may be administered to a patient, or may be found within the patient him or herself. For example, in the gastrointestinal (GI) tract, bacteria produce gases in the approximate ratios of 30% methane, 44% hydrogen, and 5% oxygen. Methane and hydrogen are flammable. Endoscopes, colonoscopies, and other GI procedural devices use ESUs, fiber-optic light sources, and other energy-emitting units during various procedures, which can ignite the methane and hydrogen. As the level of oxygen is too low to detect a response that signals an amount of oxygen which would facilitate an explosion, those known devices and methods which sense only oxygen, or sense the level of oxygen, would be futile against preventing explosions or fires.

Those known sensing medical devices, such as U.S. Pat. No. 7,291,145, also suffer from the above-described disadvantages. These devices are generally only limited to handheld cauterizers that detect the level of oxygen and shut down the energy source to the handheld cauterizer if a particular predetermined level of oxygen is detected during or immediately before the cauterizing process. These devices are only aimed at quantitatively measuring oxygen. These devices are only focused on determining the level of oxidizers in the surgical environment. As discussed, an explosion may occur within an environment having a normal concentration of oxygen. As such, these devices still would not prevent many surgical fires and combustions. Further, these devices only seek the level of oxygen; they do not identify any gases that may flammable, such as those found in universally used topical surgical site sterilization preparations and gases normally found within a patient's body.

Therefore, a need exists to overcome the problems with the prior art as discussed above.

SUMMARY OF THE INVENTION

The invention provides a gas-sensing surgical device and method of use that overcomes the hereinafore-mentioned disadvantages of the heretofore-known devices and methods of this general type and that identifies the type of gas(es) located in the proximity of the energy output of the surgical device.

With the foregoing and other objects in view, there is provided, in accordance with the invention, a gas sensing surgical assembly that includes a handheld surgical device with a body, a proximal end, a distal end, and a body length separating the proximal and distal ends, the device also having an energy input and an energy output, the energy output located at the distal end of the body, and a control switch operable to transfer energy from the energy input to the energy output. The gas sensing surgical assembly also includes a sensor that is coupled to the handheld surgical device, is in fluid communication with an outside environment, and is operable to identify at least one of a plurality of gases, the gas sensing surgical device also having an electronic gas detection circuit communicatively coupled to the sensor, the electronic gas detection circuit being operable, upon the identification of the at least one gas by the sensor, to control the energy output from the handheld surgical device. The gas-identification sensor may advantageously identify a gas or a gaseous substance, e.g., matter upon which a gas is constructed, such that the terms "gas" or "gaseous substance" shall be interchangeable.

In accordance with another feature, an embodiment of the present invention includes at least one gas intake aperture defined by the body and located proximal to the energy output and a channel defined by the body and extending from the at least one gas intake aperture, the channel placing the sensor in fluid communication with the outside environment.

In accordance with a further feature of the present invention, the channel includes a channel pressure lower than an outside environment pressure.

In accordance with another feature of the present invention, the sensor utilizes spectroscopy to identify the at least one gaseous substance.

In accordance with yet another feature of the present invention, the sensor utilizes electromagnetic spectroscopy to identify the at least one gaseous substance.

In accordance with a further feature of the present invention, the sensor utilizes infrared spectroscopy to identify the at least one gaseous substance.

In accordance with an additional feature, an embodiment of the present invention includes a memory communicatively coupled to the sensor and having at least one data structure that associates a sample gas identifier, received by the sensor, with a stored-value identifier of the at least one gaseous substance.

In accordance with yet another feature of the present invention, the sensor qualitatively identifies the at least one gaseous substance.

In accordance with the present invention a gas sensing surgical device includes an electrical medical device having a body, an energy input connected to an energy source, and an energy output located at a first end of the medical device, the electrical medical device being operable, through an electronic circuit system, to emit an amount of energy from the energy input to the energy output, the gas sensing surgical device also having a sensor coupled to the electrical medical device, the sensor being in fluid communication with an outside environment, operable to identify a gaseous substance, and communicatively coupled with the electronic circuit system, wherein the electronic circuit system controls the amount of energy emitted from the energy output when the sensor identifies the gaseous substance.

In accordance with another feature, an embodiment of the present invention also includes a suction assembly in fluid communication with the sensor, the suction assembly pulling the gaseous substance, proximal to the first end of the medical device, to the sensor.

In accordance with the present invention, a method for sensing gases during medical procedures is disclosed, the method comprising providing a handheld electrical medical device having a body, an energy input connected to an energy source, an energy output located at a first end of the medical device, an electronic circuit system operable to emit an amount of energy from the energy input to the energy output, and a gas identification sensor, the method also includes receiving a gaseous substance from a location proximal to the energy output, transferring the gaseous substance to the gas identification sensor, identifying the gaseous substance with the gas identification sensor, and reducing the amount of energy emitted from the energy output upon identification of the gaseous substance.

Although the invention is illustrated and described herein as embodied in a gas sensing surgical device and method of use, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

It is the object of the instant invention to address the aforementioned deficiencies that precipitate fires during surgical procedures that accompany the use of ESUs and other energy emitting surgical devices and to present an advance made in the art by utilizing spectroscopy methods. Specifically, the ESU may utilize infrared measurements to identify gases located within the proximity of the energy output of the ESU. Consequently, the device utilizes the identification of this gas and then interrupts or reduces power to the ESU.

In light of the advent of electrosurgical units (ESUs), which facilitate in surgeries, fires resulting from the use of these ESUs during surgical procedures pose a serious threat to patients undergoing medical procedures. Because of these fires and/or explosions, many patients incur serious burns, and unfortunately even death. The invention allows the use of electrosurgical units and other energy emitting surgical equipment that emit radio frequency (RF), ultrasound, laser, heat (such as a cautery), fiber-optic light, diathermy, and other open or closed types of energy used in medical procedures without the risk of combustion of gases and vapors commonly encountered during medical procedures.

Other features that are considered as characteristic of the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

The present invention may prevent combustion of flammable gases or vapors during medical procedures using infrared (IR) absorption spectroscopy. The invention may employ a technology such as MEMS-based IR sensors to detect flammable or combustible molecules, a gas aspiration mechanism (or vacuum tube) to collect the combustible molecules, and associated control hardware (such as a microprocessor or transistors) to shut off or attenuate the voltage or current being supplied to the electrosurgical unit or another energy-emitting medical device.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the body length of the device. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 1 is a perspective, downward-looking view of a gas-sensing surgical device in accordance with the present invention;

FIG. 2 is a close-up view of section A-A of the surgical device of FIG. 1 depicting apertures located proximal to an energy output of the surgical device in accordance with an embodiment of the present invention;

FIG. 3 is a cross-sectional side view of the surgical device of FIG. 1 showing a gas flowing downstream to a gas-identification sensor in accordance with the present invention;

FIG. 4 is a cross-sectional side view of a gas flowing downstream to a gas-identification sensor located within the surgical device in accordance with an embodiment of the present invention;

DETAILED DESCRIPTION

Figure 5:
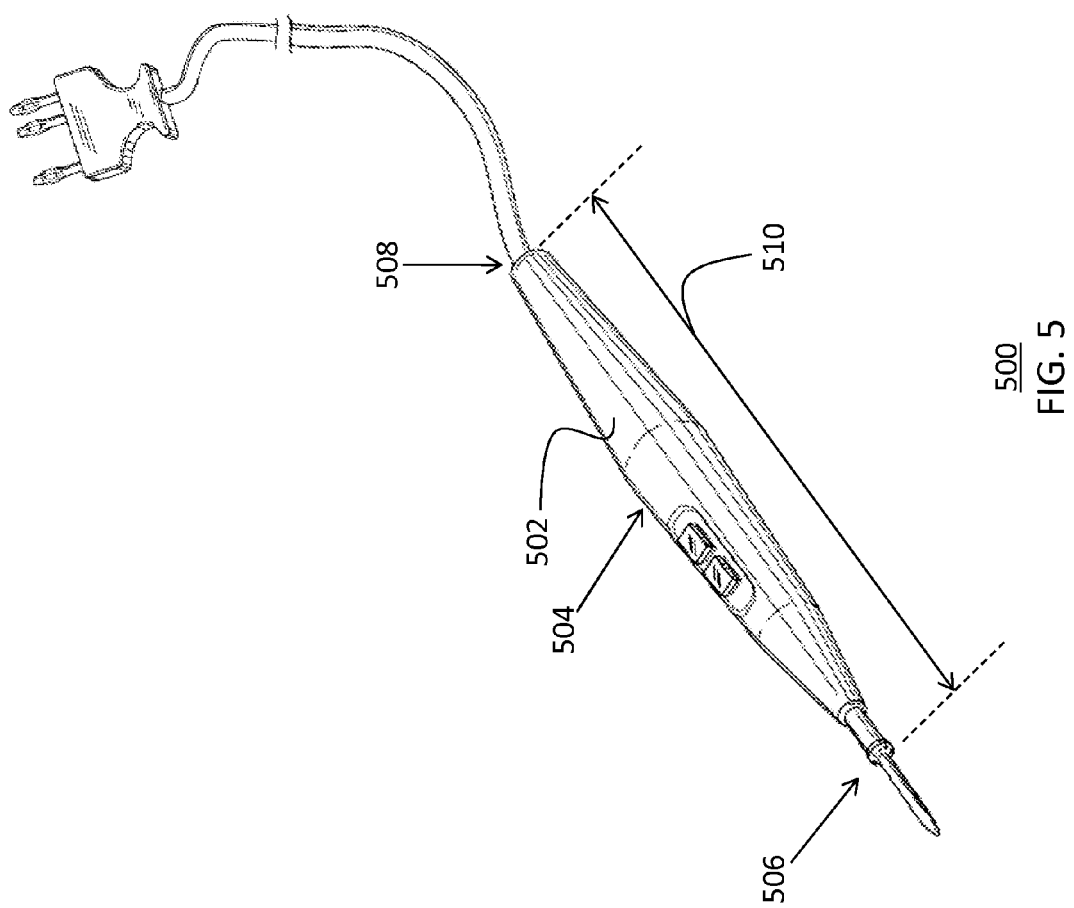
FIG. 5 is a perspective, downward-looking view of a gas-sensing surgical device with the gas-identification sensor encapsulated inside the device in accordance with an embodiment of the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient electrical surgical device that senses and identifies one or more flammable gases, subsequently terminating or reducing the amount of energy emitted from the surgical device upon detection of the gas(es). Embodiments of the invention apply the inventive sensing methodology to other medical devices that emit energy, such as various types of cauterizers, lasers, fiber-optic light sources, diathermy, ultrasounds, etc. In addition, embodiments of the invention provide a gas-sensing surgical device that may have the sensor incorporated into the body of the device or may have the sensor independent of the medical device.

Referring now to FIG. 1, one embodiment of the present invention is shown in a downward perspective view. FIG. 1 shows several advantageous features of the present invention, but, as will be described below, the invention can be provided in several shapes, sizes, combinations of features and components, and varying numbers and functions of the components. The first example of a gas-sensing surgical device 100, as shown in FIG. 1, includes a surgical device 102 (also referred to as an ESU), a sensor 106 operable to identify a gaseous substance, and an electronic circuit system 104, or an electronic gas detection circuit, is used to control the energy emitted from the ESU 102. The surgical device 102 is shown in FIG. 1 as a handheld instrument, but the present invention is in no way limited to any particular type of surgical device/instrument style. When a user desires to use the surgical device 100, in one embodiment, air is pulled from the outside environment 108 where the ESU 102 is being used and then transmitted to the sensor 106 where the gas can be identified. The sensor 106 and the electronic control system 104 are communicatively coupled by a tube 124 that carries gas from the energy output 116 to the sensor 106. As will be explained in greater detail below, the identification of a flammable or combustible gas advantageously and safely reduces or prevents energy output to the ESU 102.

In one embodiment, the ESU 102 is a handheld surgical device (capable of being supported with at least one hand of a user), also known in the art as a "surgical pencil." The construction and use of surgical pencils are well-known in the art. These pencils may be used in surgical operations to cut a patient and/or cauterize vessels. The coagulation of vessels and other tissue of the patient prevents bleeding. Moreover, these surgical pencils may be classified as cauterizing pencils, i.e., destroying tissue using heat conduction at the tip of the surgical pencil, or electro-surgical pencils, i.e., passing energy into the tissue of a patient to generate heat to melt the tissue. Regardless of the classification of the ESU 102, the present invention may be utilized with any medical device that may generate an "ignition" sufficient to cause a fire, explosion, or combustion.

As shown in FIG. 1, the ESU 102 may include a body 110 with a distal end 112 (also referred to herein as a "first end") and a proximal end 114 (also referred to herein as a "second end") and an energy output 116 located at the distal end 112 of the body 110. The ESU 102 also includes an energy input 118. It should be noted that the energy output 116 and energy input 118 do not output and receive, respectively, the same amount or type of energy. For example, the energy input 118 may receive a regulated 120VAC from a power source, while the output 116 produces a self-regulating ultrasonic blade motion or current emission. In one embodiment, the energy input 118 is located at the proximal end 114 of the body 110 and may include a cord 126 running from the body 110 to a control unit 120. In other embodiments, the energy input 118 may be located internally within the body 110 or at another portion of the ESU 102, with the ESU 102 operating off of batteries or other energy sources. The cord 126 may include electronic wiring for powering and/or controlling the ESU 102. For the ESU 102 shown in FIG. 1, the energy output 116 consists of an elongated member referred to in the art as a "blade." In one embodiment, the blade consists of a metallic material that emits a maximum current of approximately 1 ampere. In other embodiments, the type, shape, and material of the energy output 116 may vary, for example, being a flat, polymer-based material that emits ultrasonic energy/movement, which is generally known to create heat inside the tissue of a patient.

In one embodiment, the ESU 102 may have a control switch 122 that is operable to transfer energy from the energy input 118 to the energy output 116. For example, the control switch 122 may have a first position that breaks an electronic circuit, interrupting or diverting current, i.e., energy, from one conductor to another. The switch 122 may have a second position that closes the loop between two contacts, thereby transferring current to the energy output 116. The switch 122 may be operated independently of the electronic circuit system 104, or may be controlled by the electronic circuit system 104 such that the switch may be considered a "relay."

Referring now to FIG. 2, a close-up sectional A-A view of the gas sensing device 100 is shown. In one embodiment, the body 110 can be seen defining at least one gas intake aperture 200 that is located proximal to the energy output 116. The at least one aperture 200 provides an inlet for gases located in the outside environment 108 where the energy is emitted. This advantageously provides the ability to channel the gas to the sensor 106 efficiently and effectively. In other embodiments, the body 110 does not have an aperture 200. In others, it has a plurality of apertures 200, which can be located near, or a distance away from, the energy output 116. Should the ESU 102 not have an aperture 200 the sensor 106 may be directly exposed to the outside environment or the device 100 may have a tube 124 channeling gas from the energy output 116 to the sensor 106, with the body 110 not defining the apertures 200.

Referring to FIG. 3, in further embodiments, the ESU 102, more specifically the body 110, defines a channel 300 that extends from the at least one aperture 200 and places the sensor 106 in fluid communication with the outside environment 108. As such, the surgical device 100 is operable to collect and transfer gasses more effectively at the site of energy output 116, which may include any location at, or along, the output 116 that discharges energy. To increase, or induce, the flow of gas within the channel 300, the channel pressure, i.e., the internal gas pressure inside the channel 300 may be lower than the atmospheric pressure or other pressure of the outside environment 108. This may be accomplished by a vacuum pump, exhaust fan, or any other device used to reduce the pressure within the channel 300. In one embodiment, the device(s), or other component(s), including the structural components of the body 110, used to reduce the pressure within the channel 300 or pull gas to the sensor 106 may be referred to in the collective as the suction assembly. In some embodiments, the suction assembly may include the channel 300. In other embodiments, the suction assembly may not include the channel 300 and may consist of more or fewer components used to pull the gas to the sensor 106.

In one embodiment, the sensor 106 is operable to identify a particular gas (gaseous substance) within the proximity of the energy output 116. As discussed, aspiration by the suction assembly may be used to quickly and effectively transfer the gas to the sensor 106. In one embodiment, the sensor 106 may detect and compare the gas concentration of a specific desired gas within a sample, i.e., the gas from the outside environment 108, to a known stored-value sample. The sensor 106 may operate utilizing catalytic oxidation, spectroscopy, or any other method of identifying characteristics of or within a gas. Catalytic oxidation involves using a wire having a resistance, with the heat that is released from the oxidation process on the wire being measured (in the form of a resistance change) with a bridge circuit. The sensor 106 may advantageously also use spectroscopy, or the interaction between matter and radiated energy. This provides an extremely accurate and effective process of qualitatively identifying gaseous substances that are combustible. Sensors utilizing spectroscopy are known in the art, but generally include measuring the interaction of a matter with radiated energy as a function of its wavelength or frequency, often reflected as a spectrum.

Utilizing spectroscopy may be accomplished using various techniques and implementations with various types of radiated energy and interactions between the energy and the matter desired to be identified. Some of the various types of radiated energy include electromagnetic radiation (classified generally by the wavelength region of the spectrum), particle radiation (such as electrons and neutrons with the wavelength determined by the kinetic energy of the particle), and acoustic spectroscopy (such as radiated pressure waves). In one embodiment, the sensor 106 utilizes electromagnetic spectroscopy to identify the gaseous substance in the environment 108. Identifying matter utilizing the electromagnetic spectrum is generally known. Generally, however, electromagnetic waves propagate through space or matter by oscillating electric or magnetic fields. The range of frequencies for the electromagnetic waves is called the electromagnetic spectrum. These frequencies typically range from $10^{20}$ Hz (gamma rays) to $10^6$ Hz (radio waves). From high to low, these frequencies are classified as gamma rays, x-rays, ultraviolet light, visible light, infrared (IR) light, microwaves, and radio waves. Changes in electric or magnetic fields can cause change in molecules. Electromagnetic radiation can be transmitted, absorbed, or reflected by matter and each spectral region, e.g., IR light, can be used to identify or investigate the molecule depending on the amount of energy imparted to the molecule. Although there may be some quantification involved in the spectroscopy process, e.g., the absorption rate, the identification of the gaseous substance by the sensor is qualitative in nature.

In another embodiment, the sensor advantageously uses infrared spectroscopy to identify a gaseous substance. This is chiefly because the absorption of infrared light by gas molecules is unique and selective to this spectral region Infrared light typically has a frequency from $4 \times 10^{14}$ to $8 \times 10^{14}$ cycles per second. Furthermore, as most gas identification sensors are required to be placed within the flow of gas, their lifespan is typically short. IR sensors, such as the one that may be used with the present invention, can be placed in a location such that they do not directly interact with the gaseous substance. This is because the molecules of the gas react only with light associated with the sensor and not the sensor itself.

The sensor 106 may also employ various techniques used to interact with the gaseous substance. This may include absorption (measuring the fraction of energy transmitted through the material), emission (measuring the amount of energy radiated from the material to be identified), elastic scattering and reflection (measuring how incident radiation is reflected or scattered by a material), impedance (measuring the ability of matter to impede or slow the transmittance of energy), inelastic scattering (measuring the exchange energy between the radiation and the matter that shifts the wavelength of the scattered radiation), coherent and resonance (measuring or detecting molecules that are excited to a non-stationary state during an interaction and then returning to the molecule's initial state—generally utilizing lasers), and other techniques.

IR light sensors or other sensors utilizing spectroscopy methods that detect and identify a particular gas may also be used with other electrical components or features, such as amplifiers, micro electro-mechanical systems (MEMS), or nano electro-mechanical systems (NEMS). This permits the gas identification sensor to be very small and fit within very small dimensional specifications, such as a surgical device. With a brief reference back to FIG. 1, in one embodiment, the gas is transported to the gas sensor 106, which is located outside of the ESU 102, but is coupled thereto with a tube 124. The gas sensor 106 may be located within a control unit 120 wherein the identification of the gas is determined. The gas sensor 106 is communicatively coupled to the circuit 104, wherein the identification of a particular combustible or flammable gas triggers the circuit to attenuate or prevent energy transfer to the energy output 116. Energy may be supplied to the ESU 102 by standard electrical outlets, batteries, solar or other energy sources.

IR light absorption spectroscopy may be used to determine and identify a particular gaseous substance that may be flammable. This process is generally known, but in one described embodiment, the device 100 may be operated such that the gas identification sensor 106 receives air from the environment 108 proximal the energy output 116. The air may also include the gaseous substance that has been predetermined to be flammable or likely to cause explosions/fires. It should be noted that, in certain embodiments, the type and class of gaseous substance(s) desired to be identified by the user can be changed on the device 100 itself or through ancillary electronic/wireless components associated with the device, e.g., Bluetooth controls or computer application(s)/software. The sensor 106 may then propagate IR light into the gaseous substance, wherein some of the IR light will be absorbed by the molecules of the gaseous substance. Generally, when a molecule of a gas absorbs IR light, it has absorption peaks. The more complex a gas molecule, i.e., the more atoms a molecule has, the more absorption bands that will occur. Each gaseous substance has a unique absorption curve that may identify it.

In one embodiment, with respect to IR light absorption spectroscopy, some of the IR light absorbed into the gas molecule is at the natural frequency of the molecule, thereby generating what is known in the art as "resonance." This resonance causes the molecule to vigorously vibrate, generating heat. The temperature increase is proportional to the gas concentration and may be detected by a detector. In other embodiments, the IR light, or energy, transmitted through the molecule, i.e., not absorbed, will be lower than the initial energy, which may also be measured. The sensor, generally through the detector, may then convert the measured electromagnetic energy or temperature changes into electrical signals that can be interpreted by a processor. In addition to a detector, the sensor 106 may also utilize light modulators, filters, gas cells, light paths, or other known components. As such, the gas identification sensor 106 will be operable to identify various gases such as (1) Alkanes or saturated hydrocarbons, e.g., methane, ethane, propane, butane; (2) Cycloalkanes; (3) Alkenes or unsaturated hydrocarbons, e.g., ethylene; (4) Aromatics, e.g., benzene; (5) Alcohols, e.g., methanol, ethanol, propanol, iso-propyl alcohol; and (6) Amines, e.g., dimethyl amine and many other gases.

FIG. 4 illustrates a device 400 wherein the gas sensor 106 is located within the body 402 of the ESU 404. This embodiment reflects an ESUs 404 that is disposable after periods of use. After the sensor 106 detects the identity of a combustible gas, it sends a signal or other data to the circuit 406 that controls the energy emitted from the energy output 408. FIG. 5 illustrates a similar handheld surgical device 500, except that now the circuit 406 and sensor 106 are encapsulated within the body 502 of the ESU 504. Therefore, the only external component of the device 500 is now the energy source (not shown). This allows all of the controlling circuitry, software, and hardware to be located within the ESU 504 such that the device 500 may be easily transported and connected to essentially any power, or energy, source. Similar to the other embodiments of the device 100 discussed herein, the body 502 includes a first end 506, a second end 508, and a body length 510 separating the first and second ends 506, 508.

As opposed to those known surgical devices, the present invention employs a mechanism to aspirate gases found at, or within close proximity to, the site of energy discharge from surgical devices, and then uses infrared (IR) absorption spectroscopy, or other detecting means (not dependent on or related to the level of oxygen), to detect the identity of flammable or combustible gases. It then utilizes hardware such as transistors or microprocessors within a control box, which may be within or ancillary to ESU 102, that will shut off or attenuate the current or voltage to medical devices that may ignite those identified gasses. This device is compatible with various types of ESUs such as cautery, lasers, ultrasound, diathermy, fiber-optic light sources, etc., and other energy emitting surgical devices. In one embodiment, only one sensor 106 utilizing spectroscopy methods will identify a gaseous substance. In other embodiments, the spectroscopy sensors may be utilized in combination with other gas-detecting sensors, or other sensors not utilized for detecting gas, such as temperature sensors and quantitative sensors. The IR absorption spectroscopy sensor 106 may be located within or attached to the device 100, may be located outside the device 100, and/or may be located downstream of gas flow (as shown in FIGS. 3 and 4).

In one embodiment, the sensor 106 may be operable to determine one particular type of gaseous substance. In other embodiments, the sensor 106 may be operable to determine at least one of a plurality of gases, or may be operable to determine multiple gases among a plurality of gases. The above-described methods utilized by the sensors 106, e.g., spectroscopy, may be used to determine one or more gases that may be combustible or hazardous to a user or patient.

Figure 6:
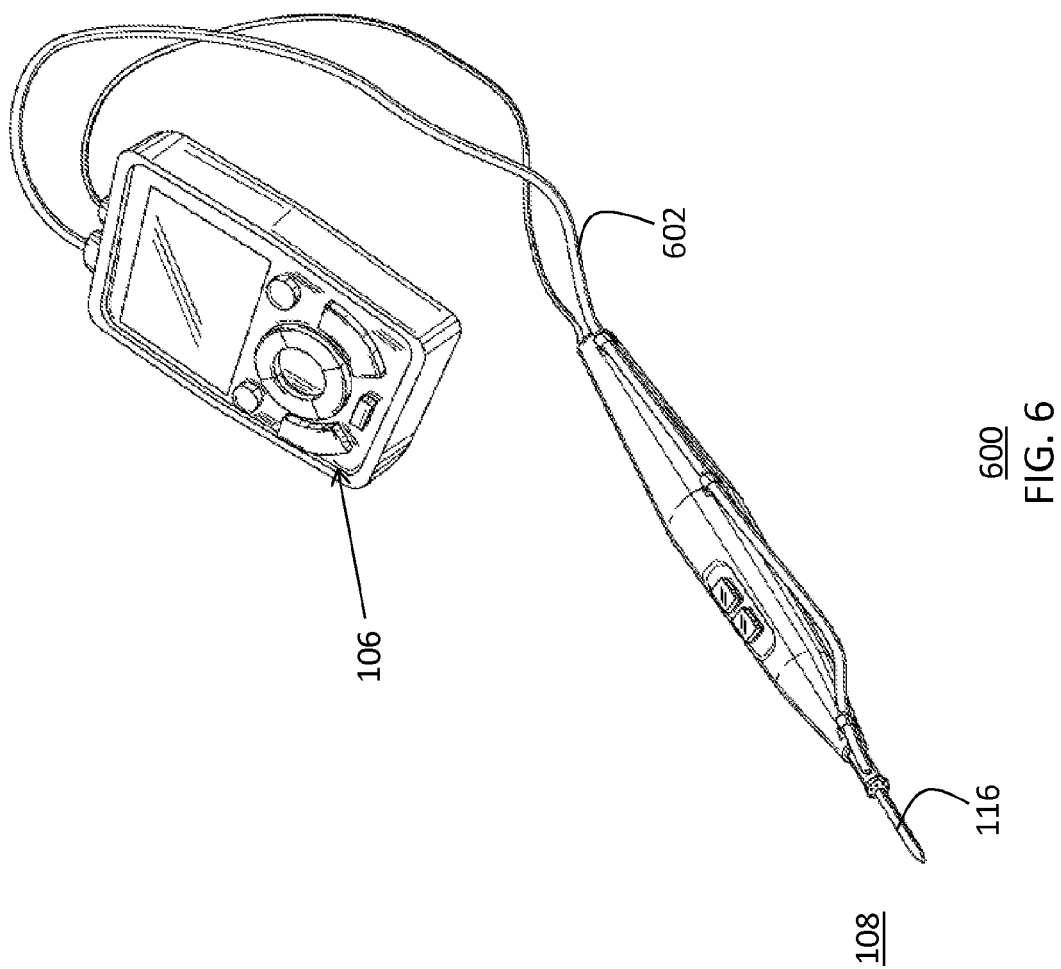
FIG. 6 is a perspective, downward-looking view of a gas-sensing surgical device with a tube extending from the environment, which is proximate to the energy output, to a gas-identification sensor located ancillary to a surgical device in accordance with another embodiment of the present invention.

With reference now to FIG. 6, another embodiment of the device 600 is shown with the gas sensor 106 located outside of the ESU 102. In the illustrated representation of the device 600, the gas proximal to the energy output 116 is relayed from the outside environment 108, through a tube 602, to an external control unit where the gas is identified by the sensor 106. As such, an ESU 102 may be quickly discarded and interchanged with a new ESUs 102 after use. This allows the more costly components of the device 600, i.e., the control unit and the sensor, to be continually employed with different ESUs 102. To facilitate the tube 602 coupling with the ESU 102, a clip, adhesive, or other method may be employed.

Figure 7:
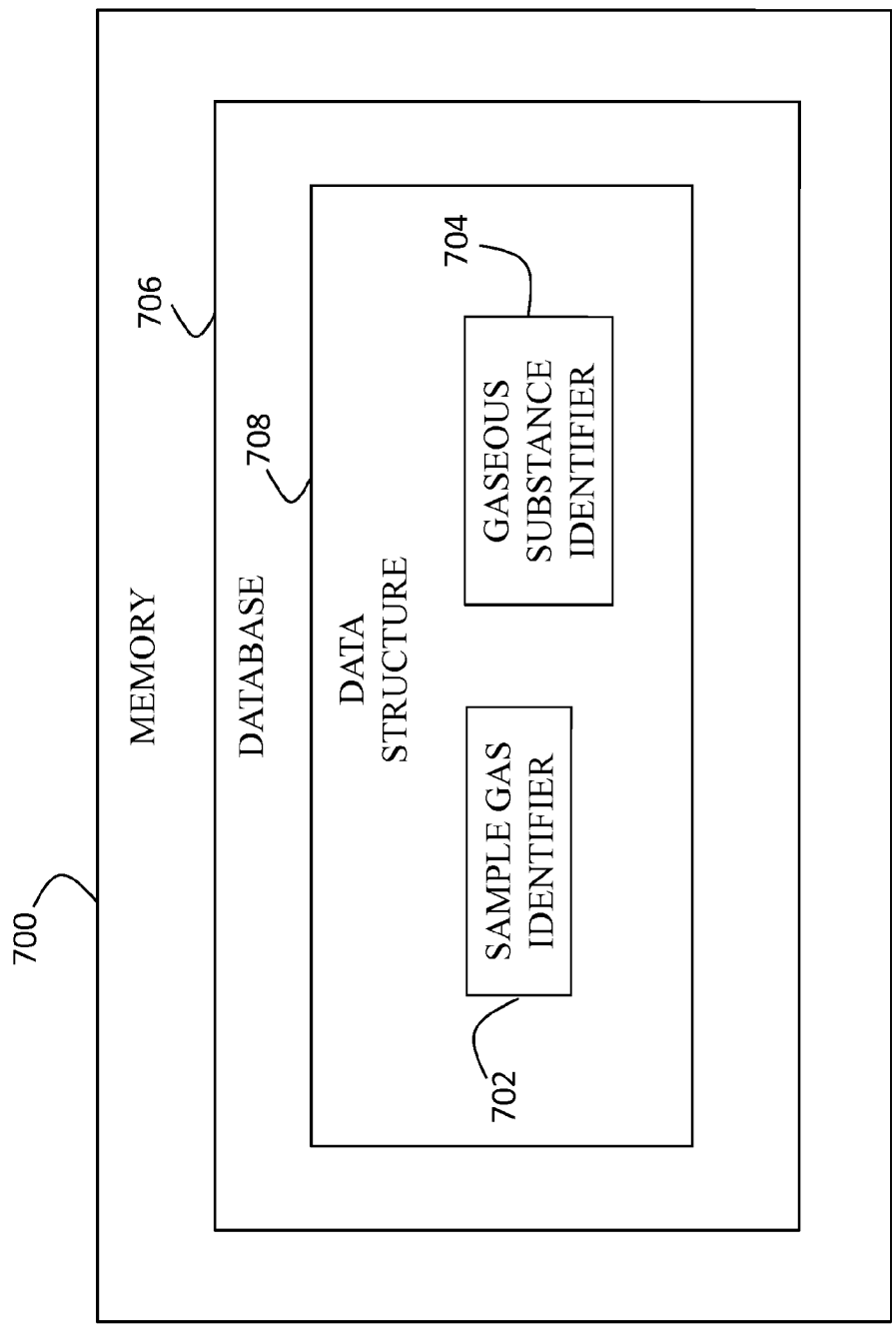
FIG. 7 is a block diagram reflecting a memory module utilized with a gas-sensing device, the memory storing a database with a data structure that includes a sample gas identifier and a gas identifier in accordance with an embodiment of the present invention.

FIG. 7 is a block diagram representing a memory 700 that may be used in accordance with an embodiment of present invention. To determine a particular gas that may be combustible or harmful, the device 100, or more specifically the sensor 106, may compare a sample gas identifier 702, such as an IR light spectrum, with a stored-value identifier 704 of a particular gas. For example, after the device 100 brings the gas from the environment 108 to the sensor 106, the sensor 106 determines what gases or gas concentrations are in the gaseous substance in the form of one or more sample gas identifiers 702. The typical alcohol IR spectrum has a broad peak from approximately 3550-3200 $cm^{-1}$, i.e., a sample gas identifier 702. This identifier 702 will then be sent by the sensor 106 to the memory 700, having a database 706, with at least one data structure 708, wherein a processor will associate the sample gas identifier 702 with the stored-value identifier 704. This method is only exemplary and the present invention may utilize other methods depending on the sensing means utilized by the device 100.

The term "data structure" is defined herein as any particular method of storing and organizing data. In one embodiment, the data structure 708 includes one or more lookup tables. In other embodiments, the data structure 708 is a B-tree, hash tables, arrays, or other methods of storing and organizing data. The memory 700 includes one or more programs that can be executed by the processor. The programs can cause the processor to carry out at least one set of instructions that include accessing and searching the memory 700.

Quickly referring back to FIG. 1, in order to control the energy output from the device 100 before the sensor 106 has had an opportunity to identify a particular gaseous substance that is combustible/flammable, the electronic circuit system 104 is communicatively coupled to the sensor. More specifically, the electronic circuit system 104 is operable to control the energy output from the ESU 102 upon receiving the identification of the gaseous substance by the sensor. Therefore, the circuit system 104 may completely limit, attenuate, maintain, or increase the energy emitting from the ESU 102 before receiving any input or identification from the sensor 106. The electrical system 104 may consist of an interconnection of electrical elements or components such as resistors, inductors, capacitors, transmissions lines, voltage sources, current sources, and switches (including the toggle switch 122), and integrated circuits, such as a microcontroller/controller. This system 104 may also incorporate components and/or features utilized in connection with the sensor 106 to control or limit the energy emitted from the ESU 102. The circuit system 104 may be located on the ESU 102 itself, or may be outside of the ESU 102.

Figure 8:
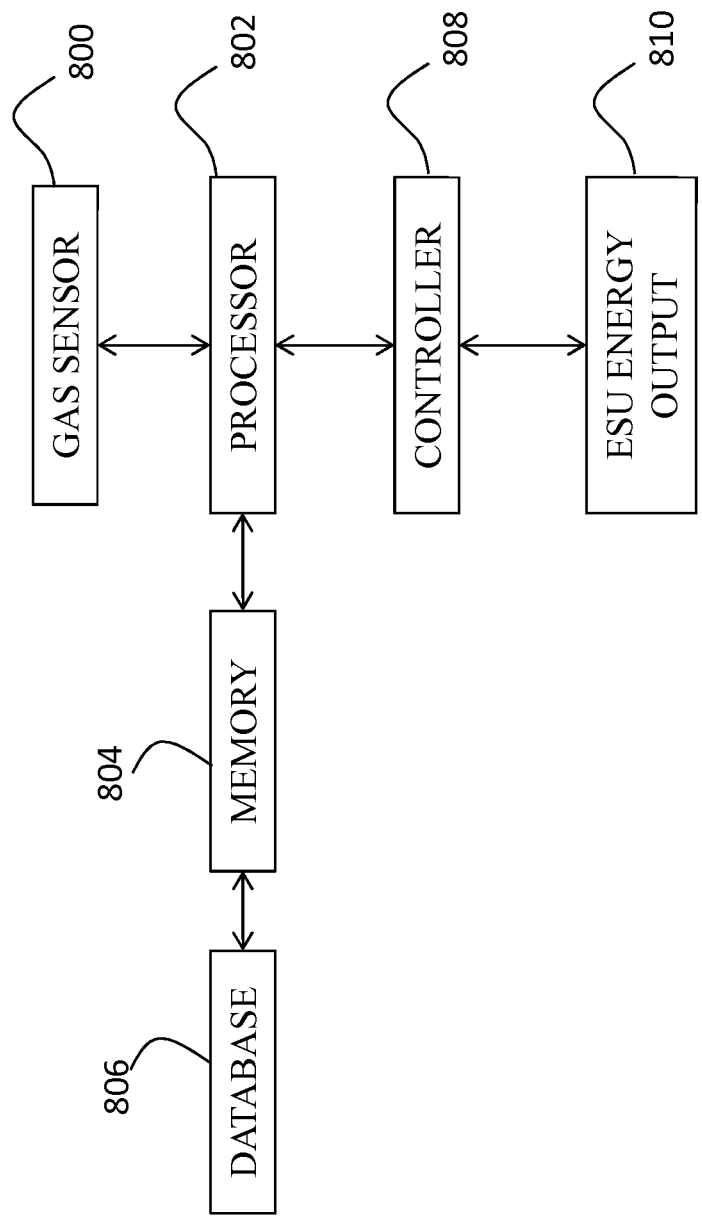
FIG. 8 is a representative block-diagram schematic of the components that can be utilized in a device to detect a gas and control the operation of the device in accordance with an embodiment of the present invention.

A schematic block diagram depicting an exemplary embodiment of these various components interconnected between each other is shown in FIG. 8. After the gas sensor 800 receives a sample gas identifier 702, this identifier 702, through the use of a processor 802, is sent to the memory 804. The memory 804 may have a database 806 with one or more gaseous substance identifier(s) 804. The processor 802 may carry-out one or more programs, stored on the memory 804, to associate the sample gas identifier 702 with the gaseous substance identifier 704. Based upon the type of gas(es) identified, a controller 808 then terminates, reduces, increases, or maintains the amount of energy emitted from the ESU output 810. This process provides an efficient and effective means to identify potentially hazardous gases, thereby preventing an energy source, i.e., the ESU 102, from facilitating combustion, and possible explosion, with those gases. As the safety and welfare of patients are enhanced, medical facilitates and physicians will also be subject to lower malpractice premiums and a reduction in civil liability.

Figure 9:
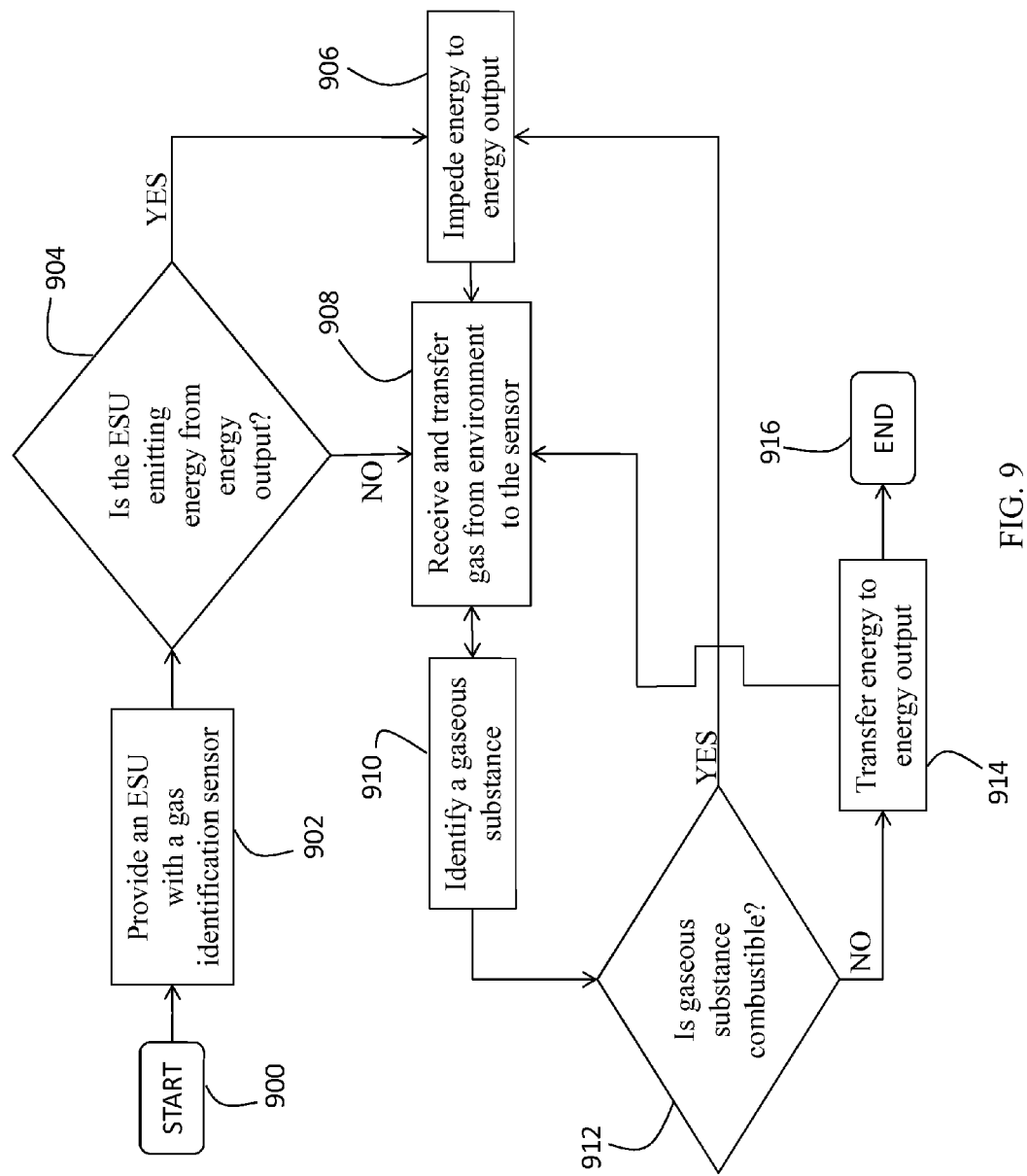
FIG. 9 is a process flow diagram representing a method of sensing one or more gases during medical procedures and controlling the operation of the device upon sensing the one or more gases in accordance with the present invention.

FIG. 9 represents an exemplary process-flow chart showing the operation of the device 100 before or while the device 100 is being operated. The process of sensing gases during medical procedures starts at step 900 and immediately proceeds to the step 902 of providing an ESU 102 with the above-identified structural features, e.g., the body 110, an electronic circuit system 104 operable to emit an amount of energy from the energy input 118 to the energy output 116, and a gas identification sensor 106. Subsequently, the process flows to the step 904 of inquiring whether the ESU 102 is currently emitting energy from the energy output 116. This may be done using one or more electrical and/or software components, such as a microcontroller. If the response to the inquiry is yes, the process goes to the step 906 of having the electrical system 104 impede or reduce the amount of energy emitted from the energy output 116. If the response to the inquiry is no, or after the device 100 has limited the amount of energy emitted from the energy output 116, the process proceeds to the step 908.

Step 908 includes receiving a gaseous substance from a location proximal to the first end 112 of the ESU 102, or proximal the energy output 116, and transferring that gaseous substance to the gas identification sensor 106. Once the gaseous substance is received by the sensor 106, the next step 910 is for the sensor 106 to identify the gaseous substance utilizing any of the above-described methods. Following step 910, step 912 includes the sensor 106 determining, possibly in combination with the electrical system 104, whether or not the gaseous substance is combustible. In other embodiments, the query in step 912 may be modified to determine if the gaseous substance is hazardous, is likely to cause or facilitate a fire, or any other parameter set by the user. If the response to the query is yes, then the process moves back to step 906 of having the electrical system 104 impede or reduce the amount of energy emitted from the energy output 116. If the response to the query is no, then the process moves to step 914, which is to transfer energy to the energy output 116.

In some embodiments, after the process has reached step 914, the process will move back to step 908 and reiterate the steps subsequently following step 908. This may be accomplished utilizing one or more components or software of the electrical system 104, such as an internal clock signal produced by a clock generator that re-checks the conditions in the environment 108 every 1-2 seconds. In other embodiments, the process may continually re-check the conditions of the environment surrounding the energy output 116, or may be set to any other interval. Following step 914, the process terminates at step 916.

A gas sensing surgical device has been disclosed that reduces or completely limits (terminates) the energy output of a medical device upon sensing a potentially hazardous gaseous substance. The device provides an efficient, programmable mechanism to allow ESUs and other surgical devices to terminate, maintain, or reduce the emission of energy while the risk of combustion of gases and vapors exists at their point of use, thereby preventing serious or life threatening burns to patients during medical procedures.

What is claimed is:

1. A gas sensing surgical assembly comprising:
   an electrical medical device having a body, an energy input connected to an energy source, and an energy output located at a first end of the medical device, the electrical medical device being operable, through an electronic circuit system, to emit an amount of energy from the energy input to the energy output; and
   an infrared spectroscopy sensor:
      coupled to the electrical medical device;
      in fluid communication with an outside environment;
      configured, without the use of additional sensors, to be electronically and selectively altered by a user to detect at least one of a plurality of gases; and
      communicatively coupled with the electronic circuit system,
   wherein the electronic circuit system reduces the amount of energy emitted from the energy output when the sensor detects the at least one of the plurality of gases.

2. The gas sensing surgical assembly according to claim 1, further comprising:
   a suction assembly in fluid communication with the sensor, the suction assembly pulling a gas, proximal to the first end of the medical device, to the sensor.

3. The gas sensing surgical assembly according to claim 1, wherein:
   the sensor qualitatively detects the plurality of gases.

4. The gas sensing surgical assembly according to claim 1, further comprising:
   a memory communicatively coupled to the sensor and having at least one data structure that associates a sample gas identifier, received by the sensor, with a stored-value identifier of at least one of the plurality of gases.

5. A gas sensing surgical assembly comprising:
   a handheld surgical device having:
      a body, a distal end, a proximal end, and a body length separating the distal end from the proximal end; and
      an energy input and an energy output, the energy output located at the distal end of the body;
   an infrared spectroscopy sensor:
      coupled to the handheld surgical device;
      in fluid communication with an outside environment;
      including at least one of a micro electro-mechanical system (MEMS) component and a nano electro-mechanical system (NEMS) component; and
      operably configured, without the use of additional sensors and with the at least one of the MEMS component and NEMS component, to be electronically and selectively altered by a user to detect a plurality of gases; and
   an electronic gas detection circuit communicatively coupled to the sensor and operable, upon an identification of at least one of the plurality of gases by the sensor, to control the energy output.

6. The gas sensing surgical assembly according to claim 5, wherein the body defines:
   at least one gas intake aperture located proximal to the energy output; and
   a channel extending from the at least one gas intake aperture, the channel placing the sensor in fluid communication with the outside environment.

7. The gas sensing surgical assembly according to claim 6, further comprising:
   a channel pressure lower than an outside environment pressure.

8. The gas sensing surgical assembly according to claim 5, further comprising:
   a memory communicatively coupled to the sensor and having at least one data structure that associates a sample gas identifier, received by the sensor, with a stored-value identifier of the at least one of the plurality of gases.

9. The gas sensing surgical assembly according to claim 5, wherein:
   the sensor qualitatively detects the plurality of gases.

* * * * *